(12) United States Patent
Soykan et al.

(10) Patent No.: US 10,076,283 B2
(45) Date of Patent: Sep. 18, 2018

(54) METHOD AND DEVICE TO MANAGE FLUID VOLUMES IN THE BODY

(71) Applicant: Medtronic, Inc., Minneapolis, MN (US)

(72) Inventors: Orhan Soykan, Shoreview, MN (US); Christopher M. Hobot, Tonka Bay, MN (US); Martin T. Gerber, Maple Grove, MN (US); VenKatesh R. Manda, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 326 days.

(21) Appl. No.: 14/539,437

(22) Filed: Nov. 12, 2014

(65) Prior Publication Data
US 2015/0250427 A1    Sep. 10, 2015

Related U.S. Application Data

(60) Provisional application No. 61/899,875, filed on Nov. 4, 2013.

(51) Int. Cl.
*A61M 37/00* (2006.01)
*A61B 5/00* (2006.01)
(Continued)

(52) U.S. Cl.
CPC ............ *A61B 5/7246* (2013.01); *A61B 5/021* (2013.01); *A61B 5/0205* (2013.01);
(Continued)

(58) Field of Classification Search
CPC ... A61M 1/1603; A61M 1/1611; A61B 5/201; A61B 5/4848
See application file for complete search history.

(56) References Cited

U.S. PATENT DOCUMENTS 3,608,729 A   9/1971   Haselden
3,669,878 A   6/1972   Marantz
(Continued)

FOREIGN PATENT DOCUMENTS

CN    0101193667    6/2008
CN    103037917    4/2013
(Continued)

OTHER PUBLICATIONS

Zoccali, Pulmonary Congestion Predicts Cardiac Events and Mortality in ESRD, Clinical Epidemiology, J. Am Soc Nephrol 24:639-646, 2013.
(Continued)

*Primary Examiner* — Leslie Deak
(74) *Attorney, Agent, or Firm* — Kenneth Collier; Roger Hahn

(57) ABSTRACT

A system and method for determining the amount of fluid to be removed from a dialysis patient is disclosed. The system utilizes sensors and a computer. The computer obtains the input parameters from the sensors, along with information added directly by the user, and performs a forward algorithm to determine a recommended change in patient fluid level. As fluid is removed, the effect of the removal on the parameters is detected by the sensors and re-transmitted back to the computer. The computer then performs a backward algorithm to refine the variables used in the forward algorithm and obtain more accurate results. The system and method provide for changing the amount of fluid removed from the patient based on the results of the algorithm and the data received from the sensors.

26 Claims, 8 Drawing Sheets

(51) Int. Cl.
*A61B 5/0205* (2006.01)
*A61M 1/34* (2006.01)
*A61M 1/16* (2006.01)
*A61M 1/28* (2006.01)
*A61B 5/021* (2006.01)
*A61B 5/024* (2006.01)
*A61B 5/046* (2006.01)
*A61B 5/053* (2006.01)
*A61B 5/08* (2006.01)
*A61B 5/1455* (2006.01)
*A61B 5/20* (2006.01)
*G06F 19/00* (2018.01)
*G16H 50/20* (2018.01)
*G16H 50/50* (2018.01)

(52) U.S. Cl.
CPC .......... *A61B 5/02405* (2013.01); *A61B 5/046* (2013.01); *A61B 5/053* (2013.01); *A61B 5/08* (2013.01); *A61B 5/14552* (2013.01); *A61B 5/201* (2013.01); *A61B 5/4848* (2013.01); *A61B 5/4875* (2013.01); *A61B 5/7264* (2013.01); *A61M 1/1603* (2014.02); *A61M 1/282* (2014.02); *A61M 1/3403* (2014.02); *G06F 19/00* (2013.01); *G06F 19/3481* (2013.01); *G16H 50/20* (2018.01); *A61B 5/4806* (2013.01); *A61M 2205/3523* (2013.01); *G16H 50/50* (2018.01)

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A | 4/1996 | Keshaviah |
| 5,651,893 A | 7/1997 | Kenley |
| 5,683,432 A | 11/1997 | Goedeke |
| 5,762,782 A | 6/1998 | Kenley |
| 5,902,336 A | 5/1999 | Mishkin |
| 5,944,684 A | 8/1999 | Roberts |
| 6,048,732 A | 4/2000 | Anslyn |
| 6,052,622 A | 4/2000 | Holmstrom |
| 6,058,331 A | 5/2000 | King |
| 6,156,002 A | 12/2000 | Hans-Dietrich |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,131,956 B1 | 11/2006 | Pirazzoli |
| 7,175,809 B2 | 2/2007 | Gelfand |
| 7,208,092 B2 | 4/2007 | Micheli |
| 7,276,042 B2 | 10/2007 | Polaschegg |
| 7,399,289 B2 | 7/2008 | Gelfand |
| 7,500,958 B2 | 3/2009 | Asbrink |
| 7,566,432 B2 | 7/2009 | Wong |
| 7,575,564 B2 | 8/2009 | Childers |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,105,260 B2 | 1/2012 | Tonelli |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |

(56) References Cited

U.S. PATENT DOCUMENTS

| | | |
|---|---|---|
| 8,696,626 B2 | 4/2014 | Kirsch |
| 8,903,492 B2 | 12/2014 | Soykan |
| 8,926,542 B2 | 1/2015 | Gerber |
| 2002/0042561 A1 | 4/2002 | Schulman |
| 2002/0112609 A1 | 8/2002 | Wong |
| 2003/0028089 A1 | 2/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0131331 A1 | 6/2005 | Kelly |
| 2005/0126998 A1 | 7/2005 | Childers |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0058731 A1 | 3/2006 | Burnett |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1* | 8/2007 | Wariar ............ A61M 1/1613 210/645 |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0215247 A1 | 9/2008 | Tonelli |
| 2008/0253427 A1 | 10/2008 | Kamen |
| 2009/0020471 A1 | 1/2009 | Tsukamoto |
| 2009/0101577 A1 | 4/2009 | Fulkerson |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1 | 1/2010 | Childers |
| 2010/0042035 A1 | 2/2010 | Moissl |
| 2010/0076398 A1 | 3/2010 | Scheurer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0264086 A1 | 10/2010 | Noack |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0259276 A1 | 10/2012 | Childers |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0250427 A1 | 9/2015 | Soykan |
| 2015/0352269 A1 | 12/2015 | Gerber |
| 2015/0367054 A1 | 12/2015 | Gerber |
| 2016/0206801 A1 | 7/2016 | Gerber |
| 2016/0331884 A1 | 11/2016 | Sigg |

FOREIGN PATENT DOCUMENTS

| | | |
|---|---|---|
| EP | 266795 A2 | 11/1987 |
| EP | 0272414 | 10/1991 |
| EP | 0330892 | 7/1994 |
| EP | 1124599 | 5/2000 |

(56) References Cited

FOREIGN PATENT DOCUMENTS

| | | |
|---|---|---|
| EP | 1175238 | 11/2000 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 2701596 | 3/2014 |
| EP | 1582226 | 1/2016 |
| JP | 2002542900 | 12/2002 |
| JP | 2003235965 | 8/2003 |
| WO | 1995003839 | 2/1995 |
| WO | 9937342 | 7/1999 |
| WO | 0057935 | 10/2000 |
| WO | 2000066197 | 11/2000 |
| WO | 2001085295 A2 | 9/2001 |
| WO | 0185295 A2 | 11/2001 |
| WO | 1085295 | 11/2001 |
| WO | 200066197 A1 | 11/2001 |
| WO | 2002013691 | 2/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004009158 | 1/2004 |
| WO | 200170307 A1 | 4/2004 |
| WO | 2004030716 A2 | 4/2004 |
| WO | 2004030717 A2 | 4/2004 |
| WO | 2004064616 A2 | 8/2004 |
| WO | 2005061026 | 7/2005 |
| WO | 2005123230 A2 | 12/2005 |
| WO | 2006011009 | 2/2006 |
| WO | 2006017446 | 2/2006 |
| WO | 2007038347 | 4/2007 |
| WO | 2007089855 A2 | 8/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009094184 | 7/2009 |
| WO | 2009157877 A1 | 12/2009 |
| WO | 2009157878 A1 | 12/2009 |
| WO | 2010028860 A1 | 2/2010 |
| WO | 2010024963 | 3/2010 |
| WO | 2010028860 | 3/2010 |
| WO | 2010033314 | 3/2010 |
| WO | 2010033699 | 3/2010 |
| WO | 2010077851 | 7/2010 |
| WO | 2010096659 | 10/2010 |
| WO | 2010121820 | 10/2010 |
| WO | 2011025705 A1 | 3/2011 |
| WO | 2011026645 | 3/2011 |
| WO | 2011137693 | 11/2011 |
| WO | 2012042323 | 4/2012 |
| WO | 2012050781 | 4/2012 |
| WO | 2012051996 | 4/2012 |
| WO | 201202073420 | 7/2012 |
| WO | 5099464 | 10/2012 |
| WO | 2012148781 | 11/2012 |
| WO | 2012148786 | 11/2012 |
| WO | 2012148787 A1 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013101292 | 7/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013101292 A3 | 10/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report dated May 26, 2015.
Wang, Fundamentals of intrathoracic impedance monitoring in heart failure, Am. J. Cardiology, 2007, 3G-10G: Suppl.
Weissman, S., et al., "Hydroxyurea-induced hepatitis in human immunodeficiency virus-positive patients." Clin. Infec. Dis, (Jul. 29, 1999): 223-224.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034334, International Search Report, dated Jul. 6, 2012.
PCT/US2012/034335, International Search Report, dated Sep. 5, 2012.
Roberts M, The regenerative dialysis (REDY) sorbent system. Nephrology, 1998, 275-278:4.
Siegenthalar, et al., Pulmonary fluid status monitoring with intrathoracic impedance, Journal of Clinical Monitoring and Computing, 24:449-451, 2010.
Zhong, et. al., Miniature urea sensor based on H(+)-ion sensitive field effect transistor and its application in clinical analysis, Chin. J. Biotechnol., 1992, 57-65. 8(1).

(56) References Cited

OTHER PUBLICATIONS

Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.

Lima, et. al., An electrochemical sensor based on nanostructure hollsndite-type manganese oxide for detection of potassium ion, Sensors, 2009, 6613-8625, 9.

Maclean, et, al., Effects of hindlimb contraction on pressor and muscle interstitial metabolite responses in the cat, J. App. Physiol., 1998, 1583-1592, 85(4).

Overgaard. et. al., Relations between excitability and contractility in rate soleus'muscle: role of the Na+—K+ pump and Na+—K—S gradients. Journal of Physiology, 1999, 215-225, 518(1).

PCT/US2012/034332, International Search Report, dated Jul. 5, 2012.

Redfield, et. al, Restoration of renal response to atria! natriuretic factor in experimental low-output heat failure, Am. J. Physiol., 1989, R917-923:257.

Rogoza, et. al., Validation of A&D UA-767 device for the self-measurement of blood pressure, Blood Pressure Monitoring, 2000, 227-231, 5(4).

Ronco et al. 2008, 'Cardiorenal Syndrome,' Journal American College Cardiology, 52:1527-1539, ABSTRACT.

Secemsky, et. al, High prevalence of cardiac autonomic dysfunction and T-wave alternans in dialysis patients. Heart Rhythm, Apr. 2011, 592-598 : vol. 8, No. 4.

Wei, et. al., Fullerene-cryptand coated piezoelectric crystal urea sensor based on urease, Analytica Chimica Acta, 2001,77-85:437.

PCT/US2014/067650 International Search Report Written Opinion dated Mar. 9, 2015.

PCT/US2012/034335, International Preliminary Report on Patentability, dated Nov. 7, 2013.

Gambro AK 96 Dialysis Machine Operator's Manual, Dec. 2012.

PCT/US2012/034329, International Preliminary Report on Patentability, dated Oct. 29, 2013.

U.S. Appl. No. 13/757,794, filed Feb. 2, 2013.
U.S. Appl. No. 13/757,722, filed Feb. 1, 2013.
U.S. Appl. No. 13/837,287, filed Mar. 15, 2013.
U.S. Appl. No. 13/757,792, filed Feb. 2, 2013.
U.S. Appl. No. 13/791,755, filed Mar. 8, 2013.

PCT/US2014/014357 International Search Report and Written Opinion.

Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

The FHN Trial Group. In-Center. Hemodialysis Six Times per Week versus Three Times per Week, New England Journal of Medicine, 2010 ABSTRACT.

U.S. Appl. No. 13/757,693, filed Feb. 1, 2013.

Coast, et al. 1990, An approach to Cardiac Arrhythmia analysis Using Hidden Markov Models, IEEE Transactions on Biomedical Engineering. 1990, 37 (9):826-835.

PCT/US2012/034330, International Preliminary Report on Patentability, dated Oct. 29, 2013.

PCT Application, PCT/US20013/020404, filed Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.

PCT/US2012/034333, International Preliminary Report on Patentability, dated Oct. 29, 2013.

PCT/US2012/034333, International Search Report, dated Aug. 29, 2013.

U.S. Appl. No. 13/757,794, filed Feb. 2, 2012.

Bleyer, et. al., Sudden and cardiac death rated in hemodialysis patients, Kidney International. 1999, 1553-1559: 55.

Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.

U.S. Appl. No. 13/424,517 IDS, filed Aug. 2, 2012.
U.S. Appl. No. 13/424,517, IDS filed Dec. 2, 2013.

PCT/US2012/034332, Internatonal Preliminary Report on Patentability, dated Oct. 29, 2013.

PCT/US2012/034303, Internationa Search Report, dated Jul. 6, 2013.

PCT/US2012/034327, International Preliminary Report on Patentability, dated Oct. 29, 2013.

John Wm Agar: "Review: Understnading sorbent dialysis systems," Nephrology, vol. 15, No. 4, Jun. 1, 2010, pp. 406-411.

Office Action in Chinese Application No. 201510593695.3 dated Jul. 12, 2017.

PCT/US2014/065201 International Preliminary Report on Patentability dated May 19, 2016.

Office Action in European Application No. EP 12717021.5 dated Feb. 3, 2017.

European Search Report for App. No. 14859115.9, dated Jan. 5, 2018.

Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.

Chinese Office Action in App. No. 201480059332.5, dated Mar. 30, 2018.

* cited by examiner

METHOD AND DEVICE TO MANAGE FLUID VOLUMES IN THE BODY

FIELD OF THE INVENTION

The invention relates to an electronic device that can monitor the fluid levels in a mammal with heart failure or kidney disease, and can support decision making regarding the amount of fluid to be removed from the subject during a hemodialysis session. The systems and methods of the invention include electronic circuits, electronic sensors, a computer processor, algorithm(s) and a telecommunications set-up. The invention further relates to methods for signal processing and patient monitoring.

BACKGROUND

Functioning kidneys of the mammals remove excess fluids, electrolytes, and other molecules. In patients with Chronic Kidney Disease (CKD), kidney function is severely compromised. Chronic kidney disease (CKD), also known as chronic renal disease, is a progressive loss in renal function over a period of months or years. The co-morbidities of CKD are diabetes and high blood pressure, which are indicated to be responsible for up to two-thirds of the cases. Heart disease and the associated cardiac arrhythmias are the leading cause of death for many people suffering from CKD. Excessive fluid, ions and other toxins accumulate in patients with CKD. Although these patients are usually treated by hemodialysis therapy, the treatment is not continuous, but periodic, causing the build-up of excessive amount of fluids in the body between hemodialysis sessions.

Fluid buildup in the body is also a concern for patients with heart failure, a debilitating medical condition in which the ability of the heart muscle to pump the blood is reduced. As the contractions of the heart become weaker and the ability of the heart to push the blood into the arteries is reduced, both the stroke volume and the cardiac output decrease. The volume of blood remaining in the veins increase, causing the fluid to build in the tissues of the subject. The ability of the kidney to excrete excess salts and water is also reduced during the heart failure, further increasing the overall fluid accumulation. Excess fluid can build up in various locations in the body, leading to a general condition known as edema. Edema may cause the swelling that occurs in the feet, ankles and the legs, in which case it is called the peripheral edema. It may also occur in the lungs as with pulmonary edema or in the abdomen as in ascites.

Fluid accumulation in the body causes multiple problems for the patient and the health care system. Peripheral edema causes local pain and discomfort. Pulmonary edema creates breathing difficulties and makes it difficult for the patients to sleep. Ascites increases the external pressure on the vena cava, resulting in the reduced blood return to the heart from the systemic circulation. The increased blood volume elevates the load on the already weakened cardiac muscle, making the heart failure even worse. The increased blood volume also increases the systolic blood pressure which worsens the kidney failure. The stretching of the thin walls of the atria due to the excess blood volume increases the incidence of atrial fibrillation. Given all the negative effects of the volume overload, fluid overload in the patients, especially for ones with kidney or heart disease, must be managed carefully. Otherwise, patients require frequent hospitalizations, which is inconvenient and costly to medical system.

Over the years, many methods have been developed to treat the fluid overload in patients suffering from cardiac and kidney failure. The methods range from pharmaceutical therapies such as the administration of diuretics to increase urine production by the kidneys to the physical methods to directly remove fluids such as ultrafiltration, hemodialysis and peritoneal dialysis. Diuretics increase the urine production by the kidneys to enhance the removal of the fluids using the residual function of the renal system. Although using diuretics reduces the fluid volumes, some patients do not respond to this therapy, either due to the resistance of their body to the drug, or due to the complete failure of their kidneys. Diuretics also contribute to a phenomenon known as the downward spiral in patients with heart failure as illustrated in FIG. 1. Briefly, the administration of diuretics 101 initially leads to the reductions in the fluid volume 102. As the fluid volume is decreased, the venous pooling of the blood is also reduced, providing some relief to the heart 103. The filling of the heart is also reduced 104 due to the lower pressure of blood in the venous system. Since the heart is not filled completely, cardiac muscle is not fully stretched; hence it does not contract vigorously, but instead produces a weak ejection 105 and 106. This once again causes increased fluid accumulation 107 in the lungs and in the other tissues, leading to the worsening of the forward heart failure 108, which is the inability of the heart to deliver adequate amounts of blood into the arteries. After repeating the cycle in FIG. 1 many times, diuretics eventually become ineffective and the symptoms of the patient can no longer be treated with the administration of additional diuretics. The situation is further illustrated in FIG. 2 where the venous return 201 and cardiac output 202 are shown as a function of the right atrial pressure 203. In that diagram, the normal venous return 204 and cardiac output 205 are shown at point 206. Fluid overload elevates the right atrial pressure, resulting in the reduction of both the venous return and the cardiac output of the patient to the point at 207. Chronic stretching of the atrial wall due to the excess fluid volumes and the increased atrial pressures lead to the onset of cardiac arrhythmias, usually in the form of atrial fibrillation.

Hence, there is a need for methods and systems that overcome the limitations of diuretics. There is also a need for methods and systems to treat the fluid overload in patients suffering from cardiac and kidney failure that overcome limitations associated with pharmaceutical therapies and physical methods to directly remove fluids such as ultrafiltration, hemodialysis and peritoneal dialysis.

SUMMARY OF THE INVENTION

The invention is directed to a method for monitoring and treatment of subjects with cardiac disease or kidney disease receiving dialysis treatment. Related medical systems, methods for the build of implantable devices and external monitoring and treatment devices are provided.

In one embodiment, the method can have the steps of obtaining one or more parameters from the patient, communicating the parameters to a medical device processor, wherein the medical device processor utilizes those parameters via a forward algorithm to generate a result, and determining the recommended patient fluid level based on the result.

In another embodiment, the method also can have the step of changing the fluid level in a patient to the recommended fluid level.

In one embodiment, the forward algorithm can compute the recommended change in fluid level in a patient wherein the recommended patient fluid level is based on one or more parameters positively correlated for fluid removal and one or more parameters negatively correlated for fluid removal.

In another embodiment, the one or more parameters positively correlated for fluid removal and the one or more parameters negatively correlated for fluid removal can be multiplied by a weighting coefficient.

In one embodiment, the one or more parameters positively correlated for fluid removal can be a function of an input parameter, an off-set coefficient, and a scaling coefficient, and the one or more parameters negatively correlated for fluid removal can be a function of an input parameter, an off-set coefficient and a scaling coefficient.

In another embodiment, the one or more parameters positively correlated for fluid removal can be selected from the group of atrial fibrillation burden, respiratory rate, sleep pattern, dialysis markers, patient weight, patient medications and dosage, patient supplied data indicative of fluid removal, and clinical data indicative of fluid removal.

In one embodiment, the one or more parameters negatively correlated for fluid removal can be selected from the group of tissue impedance, ambulatory heart rate variability, body temperature, heart rate change during dialysis, heart rate variability during dialysis, blood pressure reduction during dialysis, mixed venous oxygen saturation, and patient medications and dosage indicative of fluid retention.

In another embodiment, the forward algorithm can be computed from a function. In one embodiment, one or more of the parameters can be obtained from the patient prior to dialysis. In another embodiment, one or more of the parameters can be obtained from measurements made during dialysis.

In one embodiment, one or more of the parameters can be obtained from the patient's medical records.

In another embodiment, the parameters can be atrial fibrillation burden, tissue impedance, heart rate variability, sleep pattern and body weight.

In one embodiment, the method can also have the step of utilizing a computer to calculate the recommended fluid level in a patient.

In one embodiment, the method also can have the step of changing the fluid level in a patient to the recommended amount by ultrafiltration.

In one embodiment, the weighting coefficients, off-set coefficients and scaling coefficients can be adjusted during dialysis by using a backward algorithm and patient results.

In one embodiment, the backward algorithm can utilize data from multiple sessions of the patient.

In one embodiment, the parameter positively can be correlated for fluid removal is selected from the group consisting of pulmonary arterial pressure, venous pressure and atrial pressure.

In one embodiment, the forward algorithm can compute the function DFL=W1*D1(P1,Xi)+W2*D2(P2,X2)+ W3*D2(P3,X3)+W4*D1(P4,X4)+W5*D1(P5,X5)+W6*D2 (P6,X6)+W7*D2(P7,X7)+W8*D2(P8,X8)+W9*D2(P9, X9)+W10*D2(P10,X10)+W12*D1(P12,X12)+W13*D1 (P13,X13)+W14*D2(P14,X14)+W15*D1(P15,X15)+ W16*D1(P16,X16); where DFL is the recommended change in fluid level in a patient, W1 through W16 are weighting coefficients, X1 through X16 are cut-off triggers, P1 through P16 are input parameters, D1 is a function wherein an output is either 0 and 1 and increases from 0 to 1 as the value of the input parameter increases to a value greater than cut-off trigger, D2 is a function wherein an output is either 0 or 1 and the value deceases from 1 to 0 as the value of an input parameter is greater than the value of the cut-off trigger, wherein parameters associated with D1 correlate to an excess of fluid in the patient when increased and the parameters associated with D2 correlate to an excess of fluid in the patient when decreased.

In one embodiment, the parameters used in the method can be selected from the group comprising atrial fibrillation burden, tissue impedance, ambulatory heart rate variability, respiratory rate, sleep pattern, body temperature, heart rate change during dialysis, heart rate variability during dialysis, blood pressure reduction during dialysis, mixed venous oxygen saturation, fluid removed during dialysis session, dialysis markers, patient weight, patient medications and dosage, patient supplied data, and clinical data.

The invention can be a system for measuring the recommended change in patient fluid level. In one embodiment, the system can be made from one or more sources of parameters from a patient, a medical device processor in electronic communication with the sources of the parameters, wherein the medical device processor utilizes a forward algorithm to calculate a recommended change in patient fluid level.

In another embodiment, the system can be a computer that calculates the recommended change in patient fluid level.

In one embodiment, the forward algorithm can compute the recommended fluid level in a patient wherein the recommended fluid level is based on one or more parameters positively correlated for fluid removal and one or more parameters negatively correlated for fluid level.

In one embodiment, the computer can determine the recommended change in patient fluid level by a forward algorithm given by the function $$DFL = \sum_{i=1}^{n} Wi * Sx(Pi, Ci, Ki)$$

wherein DFL is the recommended change in fluid level, P1 through Pn are input parameters, Sx is one of the group consisting of S1, S2, and S3, S1 is a function wherein the output is between 0 and 1 and increases as the value of the input parameter increases, S2 is a function wherein the output is between 0 and 1 and the value deceases as the value of the input parameter increases, S3 is a function wherein the output is between 0 and 1 and the value increases as the value of the input parameter varies from a set point, Sx is S1 where the parameter is positively correlated to fluid removal, Sx is S2 where the parameter is negatively correlated to fluid removal, Sx is S3 where the parameter correlates to fluid removal as it deviates from a set point, W1 through Wn are weighting coefficients, C1 through Cn are off-set coefficients, K1 through Kn are scaling coefficients, and n is the number of parameters.

In one embodiment, n can be between 5 and 100.

In one embodiment, the one or more parameters positively correlated for fluid removal can be selected from the group consisting of atrial fibrillation burden, respiratory rate, sleep pattern, dialysis markers, patient weight, patient medications and dosage, patient supplied data indicative of fluid removal and clinical data indicative of fluid removal.

In one embodiment, the one or more parameters can be positively correlated for fluid removal includes pulmonary arterial pressure, venous pressure or atrial pressure.

In one embodiment the one or more parameters negatively correlated for fluid removal can be selected from the group consisting of tissue impedance, ambulatory heart rate variability, body temperature, heart rate change during dialysis, heart rate variability during dialysis, blood pressure reduction during dialysis, mixed venous oxygen saturation, and patient medications and dosage indicative of fluid retention.

In one embodiment, the one or more sources of parameters used in the system can be measurements from an implantable device.

In one embodiment, the one or more sources of parameters used in the system can be manually entered data.

In one embodiment, the one or more sources of the parameters used by the system can be measurements taken from the patient prior to dialysis.

In another embodiment, the system further can be a signaling mechanism to signal when there is a recommended change in the patient's fluid level.

Other objects, features and advantages of the present invention will become apparent to those skilled in the art from the following detailed description. The detailed description and specific examples, while indicating some embodiments of the present invention are given by way of illustration and not limitation. Many changes and modifications within the scope of the present invention may be made without departing from the spirit of the invention.

DETAILED DESCRIPTION OF THE INVENTION

Figure 1:
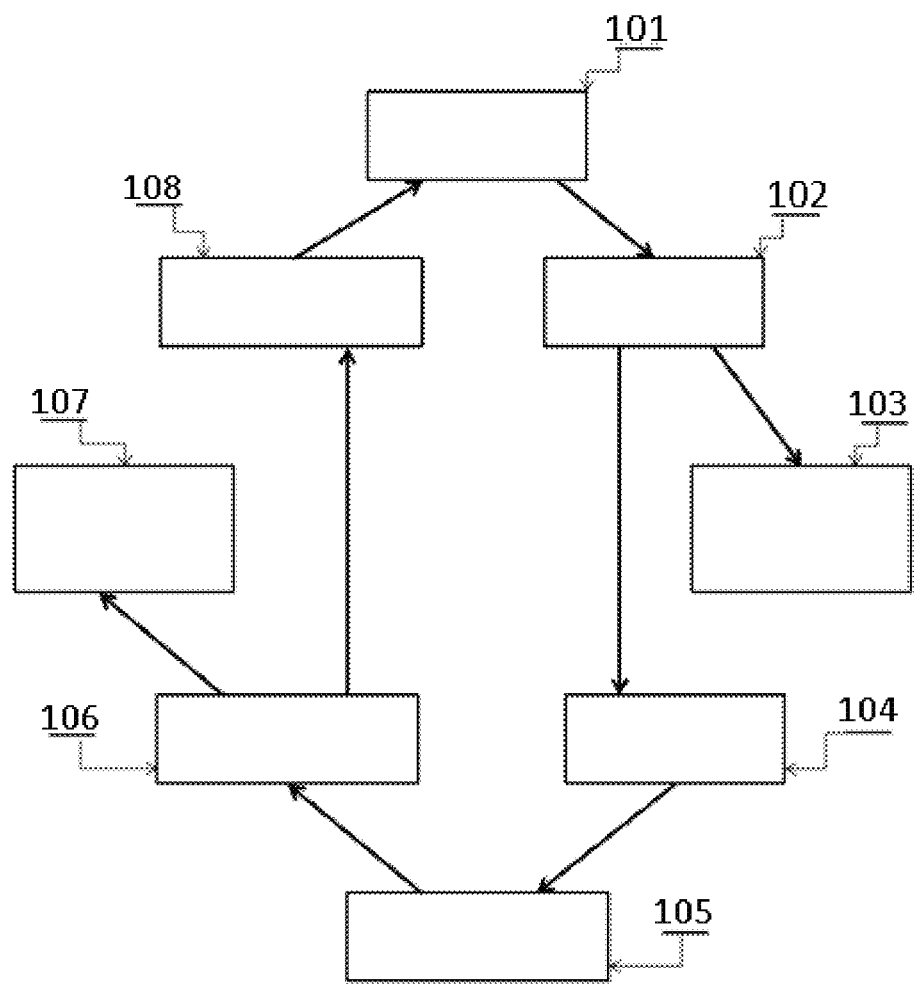
FIG. 1 is a block diagram of events describing the downward spiral in patients with heart failure.
Figure 2:
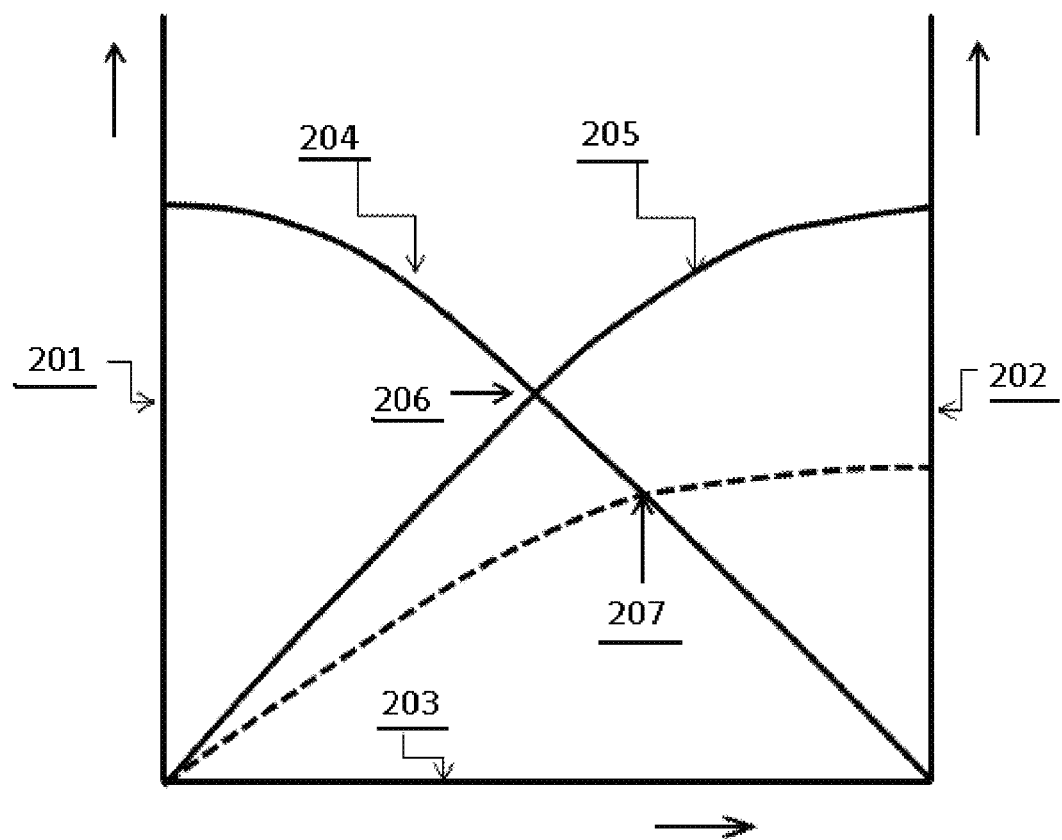
FIG. 2 is a graphical illustration of changes in the pumping function of the mammalian heart during fluid overload.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "backward algorithm," describes a series of steps or protocols whether computer implemented or not, that can affect one parameters and be correlated back to additional individual parameters.

"Chronic kidney disease" (CKD) is a condition characterized by the slow loss of kidney function. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail completely.

The terms "communicate" and "communication" include but are not limited to, the connection between the electrical elements of the system, either directly or wirelessly, using optical, electromagnetic, electrical, acoustic or mechanical connections, for data transmission among and between said elements.

The term "comprising" includes, but is not limited to, whatever follows the word "comprising." Use of the term indicates the listed elements are required or mandatory but that other elements are optional and may or may not be present.

The term "consisting of" includes and is limited to whatever follows the phrase the phrase "consisting of." The phrase indicates the limited elements are required or mandatory and that no other elements may be present.

A "control system" consists of combinations of components that act together to maintain a system to a desired set of performance specifications. The performance specifications can include sensors and monitoring components, processors, memory and computer components configured to interoperate.

A "controller" or "control unit" is a device which monitors and affects the operational conditions of a system. The operational conditions are typically referred to as output variables of the system, which can be affected by adjusting certain input variables.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed.

An "electrocardiogram" or "ECG" is a time varying waveform, produced by the electrical activity of the cardiac muscle and the associated electrical network within the myocardium. Term is used interchangeably for the ECG tracing available from an external ECG recording, or from an implantable device recording.

The term "forward algorithm" describes an series of step, procedures or protocols whether computer implemented or not, used to convert data from information sources into a value.

"Heart failure" (HF) is a condition characterized by the loss of the pumping function of cardiac muscle. The most common causes of HF are coronary artery disease, high blood pressure, diabetes and obesity. Although it can be managed for extended periods of time, there is no known cure.

A "medical device processor" refers a special purpose processor that can have any one of the following functions of controlling the collection of external or implantable medical device data, controlling the collection of metadata based on the collected data of any type, synchronizing data, and combinations thereof.

A "patient" is a member of any animal species, preferably a mammalian species, optionally a human. The subject can be an apparently healthy individual, an individual suffering from a disease, or an individual being treated for an acute condition or a chronic disease.

The term "parameters positively correlated for fluid removal" are defined as the parameters shown in Table 1 having a "+" sign in the third column and signify an additive effect on an equation. The term "parameters negatively correlated for fluid removal" are defined as the parameters shown in Table 1 having a "−" sign in the third column and signify a subtractive effect on an equation.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture and being capable of carrying out a set of commands, automatically.

The term "sensory unit" refers to an electronic component capable of measuring a property or condition of interest.

The terms "treating" and "treatment" refer to the management and care of a patient having a pathology or condition. Treating includes administering one or more embodiments of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

Components of the Invention

The present invention comprises the following components: A set of information sources including the sensors on implantable or external devices to monitor the physiological condition of the patient, a computing unit to process the information, and a communication system to relay the information between the sensors, the processing unit, the patient and the medical care personnel.

Unless specifically stated otherwise, as apparent from the foregoing discussions, it should be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses and/or devices for performing the operations herein. An apparatus may be specially constructed for the desired purposes, or it may comprise a general purpose device selectively activated or reconfigured by a program stored in the device. In yet another exemplary embodiment, the invention may be implemented using a combination of any of, e.g., but not limited to, hardware, firmware, and software, etc.

The methods, software and hardware described herein can be embodied in or use transitory or non-transitory computer readable media with instructions that cause a programmable processor to carry out the techniques described herein. A "computer-readable medium" includes but is not limited to read-only memory, Flash memory, EPROM and a magnetic or optical storage medium. A non-transitory computer readable medium includes all computer readable media except for a transitory, propagating signal.

Information Sources

Figure 3:
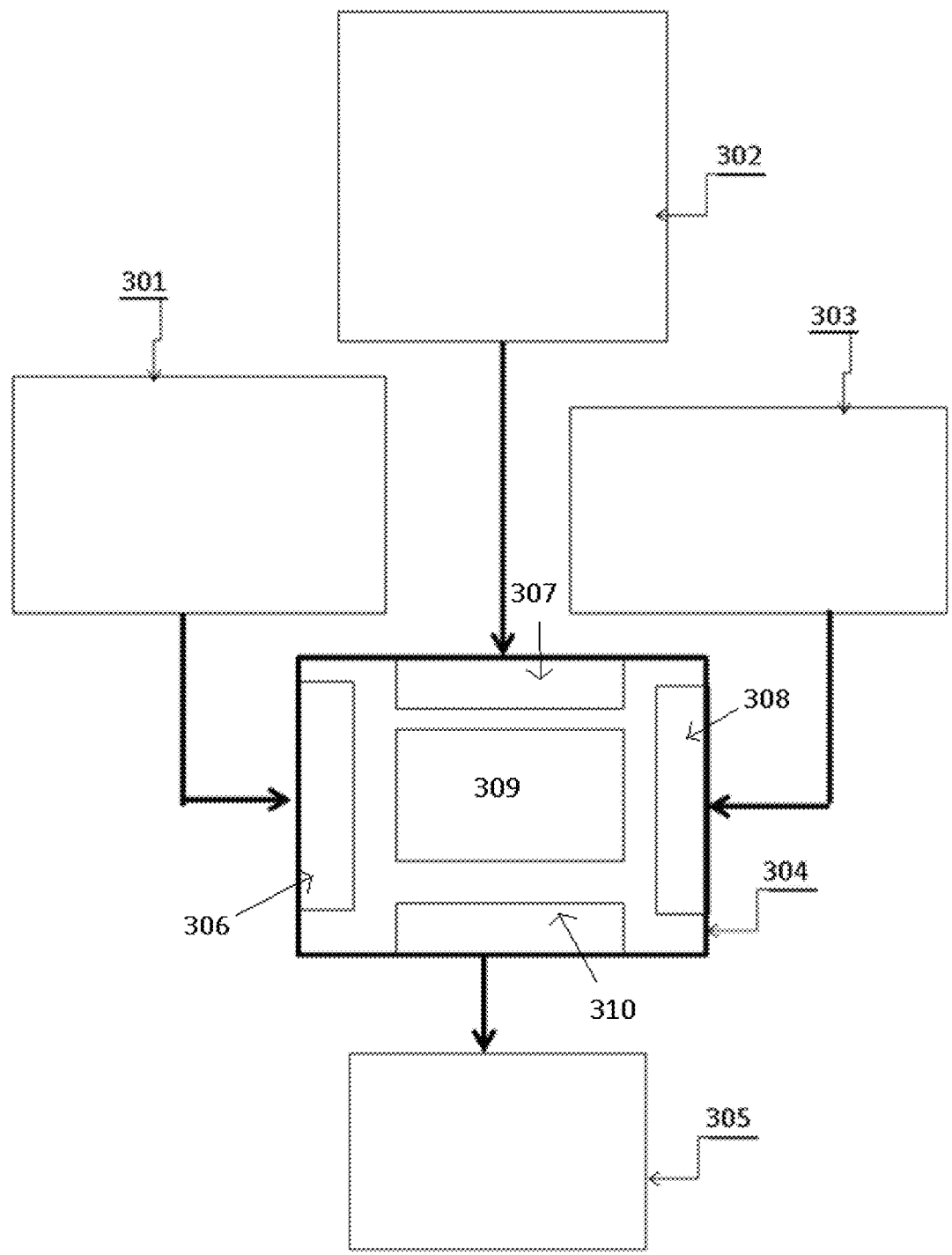
FIG. 3 is a block diagram showing the utilization of the sensory data obtained from the transducers used by the present invention.

Sensors used in the present invention provide the sources of data necessary for the processing unit to interpret. As shown in FIG. 3, they are grouped in three categories:

Category 1 of the Information Source is the data that may be obtained from an implantable device 301. This category includes the atrial fibrillation (AF) burden, tissue impedance, heart rate variability (HRV), respiration, sleep pattern and body temperature. Their relevance and utility in fluid management are described herein. Although these measurements can be obtained by an implantable medical device, external sensors may alternatively be utilized to obtain accurate readings.

AF burden increases as the fluid retention increases since extra fluid in the circulatory system stretches the atria triggering episodes of atrial fibrillation. Hence, an increase in AF burden indicates a need for additional fluid removal. AF burden can be measured by an implantable device monitoring the ECG of the patient. Alternatively, AF burden can be measured using an external device to monitor the ECG of the patient. Normally, AF episodes last less than 5 minutes and occur less than 1% of the time. Longer or more frequent episodes are indicative of a need for additional fluid removal as would be recognized by one of ordinary skill in the art.

Tissue impedance decreases as the fluid retention increases because extra fluid in the body reduces the tissue impedance. Hence, a decrease in the tissue impedance indicates a need for additional fluid removal. Tissue impedance can be measured by an implantable device monitoring the electrical impedance between two electrodes. Tissue impedance that is less than the patient's median tissue impedance measured over time would indicate a need for additional fluid removal. While changes in salt concentration do lower tissue impedance, the majority of impedance change is due to changes in fluid levels.

Heart rate variability decreases as the fluid retention increases since extra fluid in the body increases the heart failure. Hence, a decrease in the heart rate variability indicates a need for additional fluid removal. Heart rate variability can be measured by an implantable device monitoring the ECG of the subject, or alternatively an external device that measures the ECG of the subject. A peak ambulatory HRV of less than 0.15 Hz would be indicative of a need for additional fluid removal.

Respiratory rate increases as the fluid retention increases since extra fluid in the lungs reduces the tidal volume. Hence, an increase in the respiratory rate indicates a need for additional fluid removal. Respiratory rate can be measured by an implantable device monitoring the tissue impedance of the subject. A respiratory rate of more than 15 breaths per minute may be indicative of a need for additional fluid removal.

Sleep pattern is disturbed as the fluid retention increases since extra fluid in the lungs reduces the tidal volume and increases the pulmonary edema. Hence, a disturbance in the sleep pattern indicates a need for additional fluid removal. Sleep patterns can be measured by an implantable device monitoring the physical activity the subject during nocturnal hours. Normally, REM and non-REM sleep alternates every 90 minutes. Higher frequency of these changes can be indicative of a need for increased fluid removal.

The period in which the patient is asleep may be determined in other ways. In other embodiments, a patient programming device may allow the patient to signal to the implantable device that the patient is attempting to sleep. Alternatively, the period during which the patient is asleep may be determined by using an accelerometer in the implantable device. When the accelerometer determines little or no movement for a threshold period of time, it can determine that the patient is asleep. Another embodiment can include determining patient sleep patterns by the changes in heart rate and other known factors indicative of stages of sleep. Alternatively, the implanted device can determine the patient's posture, wherein a patient lying down for a threshold period of time is assumed to be asleep.

Body temperature consistently low can indicate fluid retention. Hence, a persistent drop in the body temperature can indicate a need for additional fluid removal. Body temperature can be measured by an implantable device monitoring the temperature. It can also be monitored by external thermometer. A body temperature below 36 degrees Celsius may be indicative of a need for additional fluid removal.

In some embodiments, the implantable medical devices may be compatible with the processor used to calculate the recommended change in patient fluid level, and may be set to automatically send collected data to the processor wirelessly. In other embodiments, the information may be read by a user, and manually entered into a computer for processing.

Similarly, where measurements are taken by sensors external to the patient, the sensors may automatically input the data into the computer through wired or wireless communication, or the information can be obtained by the user and manually entered.

Category 2 of the Information Source is data obtained during a dialysis session 302. This category includes the heart rate, heart rate variability, blood pressure, mixed venous oxygen saturation, amount of fluid removed, measured blood markers and body weight. Their relevance and utility in fluid management are explained below.

Heart rate is expected to drop during a dialysis session as fluid is removed from the body. An insufficient drop in heart rate during a dialysis session may indicate a need for additional fluid removal. Heart rate can be monitored by an implantable or an external device, such as an ECG monitor, blood pressure monitor or a pulse oximeter during a dialysis session. A heart rate drop of less than five beats per minute may be indicative of a need for additional fluid removal.

As described herein, the heart rate variability (HRV) is a function of the fluid levels. As the fluid is removed from the patient during a dialysis session, one of ordinary skill would expect the HRV to increase. Therefore, an insufficient increase in HRV during a dialysis session may indicate a need for additional fluid removal. HRV can be monitored by an implantable or an external device, such as an ECG monitor, blood pressure monitor, a pulse oximeter during a dialysis session, or other known devices sufficient for the intended purposes known to those of ordinary skill Heart rate variability during dialysis that is less than 0.15 Hz may be indicative of a need for additional fluid removal.

Blood pressure (BP) can be a function of the fluid levels. As the fluid is removed from the patient during a dialysis session, one of ordinary skill might expect the BP to decrease. Therefore, an insufficient decrease in BP during a dialysis session may indicate a need for additional fluid removal. BP can be monitored by an implantable or an external device during a dialysis session. A decrease in blood pressure of less than 10 mm Hg may be indicative of a need for additional fluid removal.

Another measurement of vascular pressure is the pulmonary arterial, venous (central or peripheral) or atrial pressure obtained from an implanted sensor(s) or derived from a non-implanted external sensor system. An increase in pulmonary artery pressure (diastolic, systolic or mean); central venous pressure or atrial pressure is usually a strong indicator of elevated vascular volume following excess fluid build-up.

A decrease in the mixed venous oxygen saturation may be due to inadequate oxygen delivery, caused by depressed cardiac output resulting from decreased preload, abnormal afterload and cardiac arrhythmias. It could also be due to increased end organ oxygen extraction due to higher metabolic demand, such as sepsis, fever, increased work of breathing and agitation. Hence, a decrease in mixed venous oxygen saturation, absent fever and difficulty of breathing may indicate a need for additional fluid removal. Mixed venous oxygen saturation can be measured by the dialysis system using the blood going into the dialysis system. A mixed venous oxygen saturation of below 68 mm Hg may be indicative of a need for additional fluid removal. Whether or not the patient has a fever may be determined by measuring body temperature through an implantable medical device or external thermometer.

Fluid removed during a dialysis session can be usually predetermined, but may be changed during the session if the patient experiences a hypotensive episode. Hence, the total fluid removed is a parameter to be recorded during the dialysis so it can be adjusted based on the output of the fluid management algorithm 310. This parameter may be automatically entered by the dialysis system into the computer, or alternatively, the user may determine the amount of fluid removed and manually enter it into the computer.

Both the fluid overload and the changes in serum creatinine can be independently correlated with the mortality of the patients. Hence, any increase in creatinine would increase the chances of mortality for the patient, and one can reduce the fluid volumes to compensate for the increased chance of mortality. Therefore, an increase in creatinine may indicate a need for additional fluid removal. Creatinine levels can be obtained from the blood analysis done periodically, such as once a month.

A rapid increase in patient weight can indicate increased fluid retention. Hence a sudden raise in the body weight measurement might necessitate an increase in fluid removal. Weight measurements can be done during dialysis sessions. A change in patient weight of more than 2 kilograms may be indicative of a need for excess fluid removal.

Much of the category 2 information may be obtained from an implantable medical device. In other embodiments, the information may be obtained from external sensors and measurements. In some embodiments, the external sensors can be directly attached to the dialysis apparatus, thus facilitating easy collection of information. In other embodiments, external sensors may be in electronic communication with a computer to automatically add information to the algorithm calculating the recommended change in patient fluid level. In other embodiments, the data obtained from these sensors may be manually added into the computer.

Category 3 of the Information Source 303 can be data entered manually or transferred electronically from other medical information sources, such as an electronic medical record (EMR) system. This category includes the medications taken by the patient, information supplied by the patient and a set of clinical data. Their relevance and utility in fluid management are described herein.

Medications taken can usually change the ability of the patient to excrete urine, hence alters the fluid retention. For example, a patient who can no longer tolerate diuretics will often have their doses of the diruretic reduced, leading to increases in the fluid retention. In such a situation, the fluid removal rate must be increased. Medications taken and their dosage can be manually entered or transferred from the EMR.

Patients themselves can provide information on their health conditions. For example, they may report they are having difficulty in sleeping or running out of breath when climbing stairs, indicating an increase in the fluid retention. In such a situation, the fluid removal rate must be increased. Patient supplied information can be manually entered either by the patient or the medical care personnel.

Clinical information regarding the patient can provide insights into the overall health of the subject. Recent hospitalizations due to pulmonary insufficiency could be due to fluid retention. Blood markers measured at the clinic such BNP can assess the condition of the heart failure, where an increase in BNP values would warrant the removal of additional fluids. Clinical information can be entered manually or transferred from the EMR.

Table 1 provides a summary of the variables, also called "parameters," as defined herein, their sources and correlations between the parameter and the changes recommended to the amount of fluid to be removed from the patient.

The input parameters including information from category 1, category 2, and category 3, may be communicated to a processor 304 and are shown by 306, 307 and 308 respectively. The processor 304 can operate the algorithm described below 309 to determine a recommended change in fluid level 310, which is then communicated to the system or the user 305.

Figure 4:
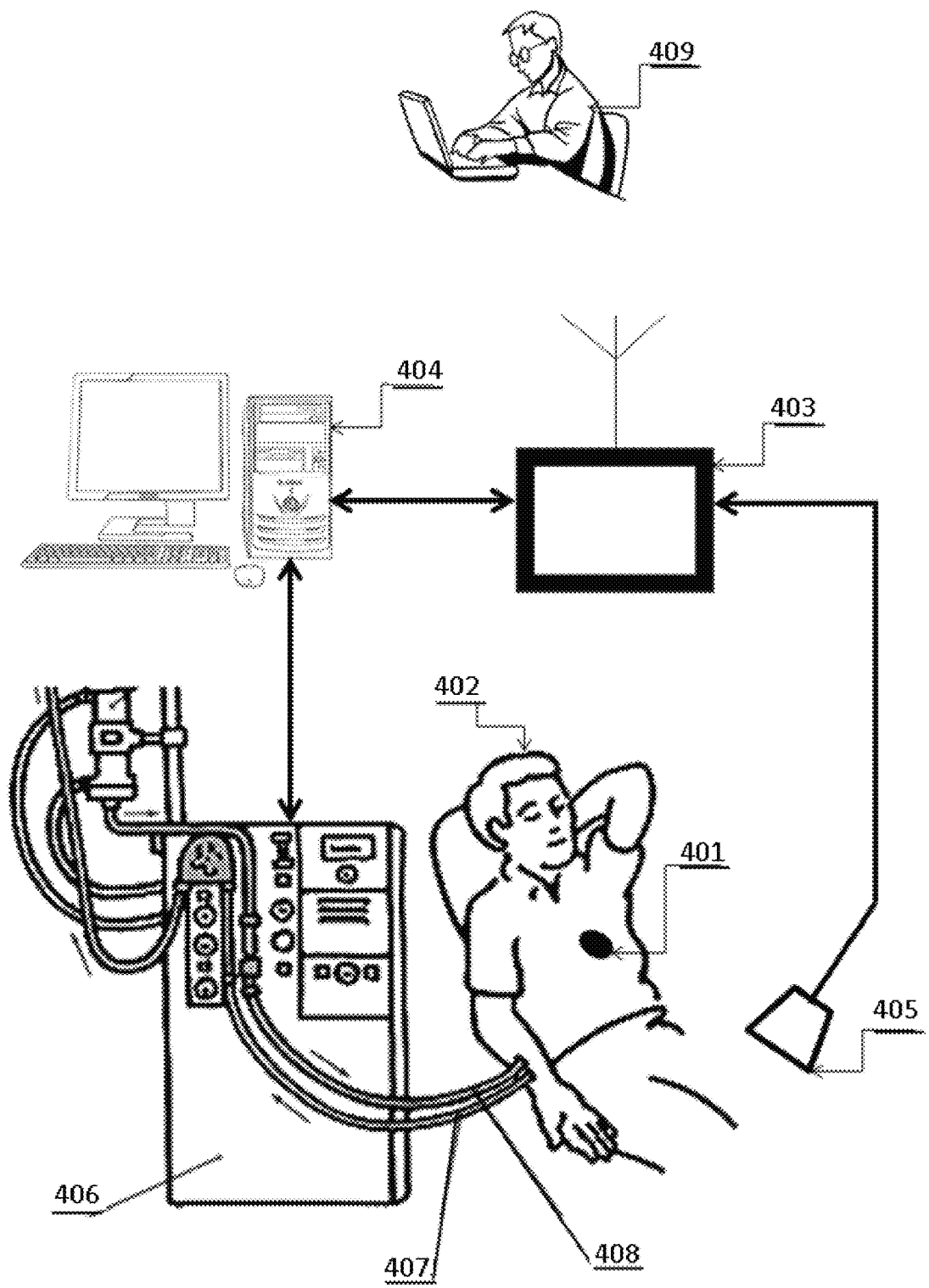
FIG. 4 is a schematic drawing of the invention.

One embodiment of the system used for determining a recommended change in patient fluid level is shown in FIG. 4. Implantable medical device 401 may be a unit with no leads or may contain leads and external sensors. Units with no leads, such as the Medtronic Reveal device, may have electrodes for sensing electrograms and tissue impedance or for stimulating. Units with leads, such as pacemakers, cardiac resynchronization devices and defibrillators, utilize their leads for sensing electrograms. Implantable medical device may also have other sensors, such as an internal or external accelerometer, temperature sensor, and external pressure sensor, which are external to the device, yet still inside the patient 402. Implantable device may contain a power source such as a battery, a computing hardware, or a data storage unit such as electronic memory and communication hardware. Implantable medical device 401 provides the information in category 1 or category 2. Category 1 or category 2 information from the implantable device 401 can be received via telemetry by a receiver unit 403 and conveyed to the computing unit 404. Alternatively, the information may be read by the user with an external receiving unit, who will manually enter the data into the computer.

External sensors 405, such as the blood pressure sensor, are placed on the patient 402 for the duration of the dialysis session. Dialysis can be provided with a hemodialysis system 406 connected to the patient 402 via blood lines 407 and 408. Hemodialysis system 406 can be in communication with a computing unit 404, such as a computer. External sensors 405 may also provide the information in category 1 or category 2. The information from the external sensors 405 can be collected by the receiver unit 403 and conveyed to the computing unit 404. Alternatively, the user may directly obtain the information collected by the external sensors and manually enter the information into the computing unit.

Category 3 information may be entered manually by a human 409 or retrieved from the Electronic Medical Records.

Examples of sources of information on the parameters are shown in Table 1. One skilled in the art will understand that these are merely examples of the sources of information and that the data may be obtained from other devices and other sources.

Computing Unit and Algorithm

The processing of the information collected in all three categories is performed by the computing unit. The computing unit can be a specially adapted unit in order to carry out the purposes and steps described herein. In any embodiment, the sensors described herein can operate in combination or conjunction with circuitry specially adapted to the purposes or steps described herein, or in combination or conjunction with more than one such processor, or in combination or conjunction with one or more elements of each type, such as for distinct steps or portions thereof. The computing unit and the sensors which detect the data in each of the categories are specifically adapted computers and processors configured or a medical or healthcare setting. The computers or processors can have shielded circuitry to prevent electric shock to a patient or operator. In any embodiment, the computers and processors of the present invention are not general purpose computers and can have regulatory approval for approved medical use on patients.

An algorithm called the "forward algorithm" is used to convert the data from the information sources into a fluid removal indicator, which will be described herein by Example 1.

EXAMPLE 1

Initially, a set of scores can be calculated from the sensory information, using one of the six functions listed in Table 2. A graphical representation of the same six functions is shown in FIGS. 5 and 6. Functions D1, D2 and D3 are discrete functions, which give discrete outcomes of zero or one, whereas, the functions S1, S2 and S3 are continuous functions with the possibility of giving any outcomes in the range from zero to one, such as 0.34. Functions D1, D2 and D3 have the advantage of being easier to implement because the only requirement is a comparison of the argument x to a threshold value of $x_C$, hence the functions D1, D2, and D3 are easier to implement in a computer. However, the discrete functions D1, D2, and D3 provide no grey scale information or proportional response to a given input. Continuous functions S1, S2 and S3 provide a much more graded response, but impose a heavier computational burden on the computer by either requiring a mathematical computation of the equation provided in Table 2 or requiring the use of a look-up table.

Figure 5A:
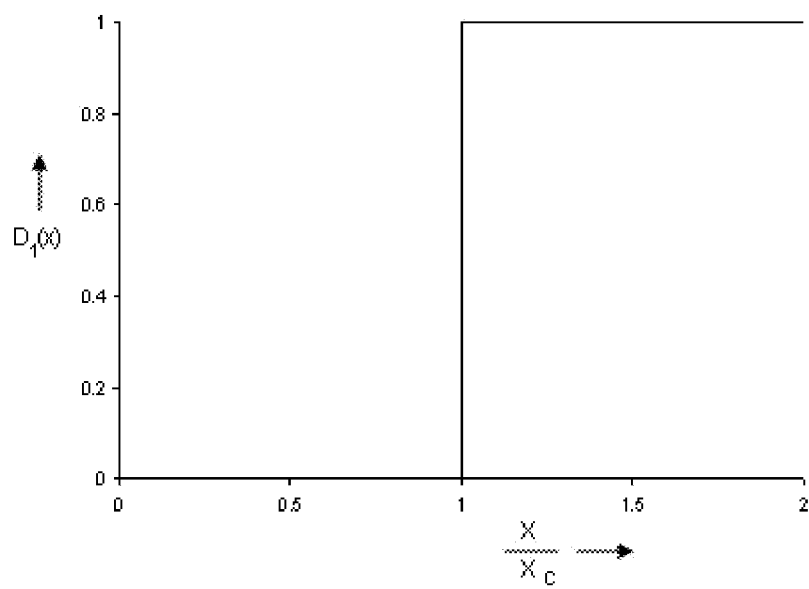
FIG. 5a is a discrete function converting information into scores for $D_1(x)$.
Figure 5B:
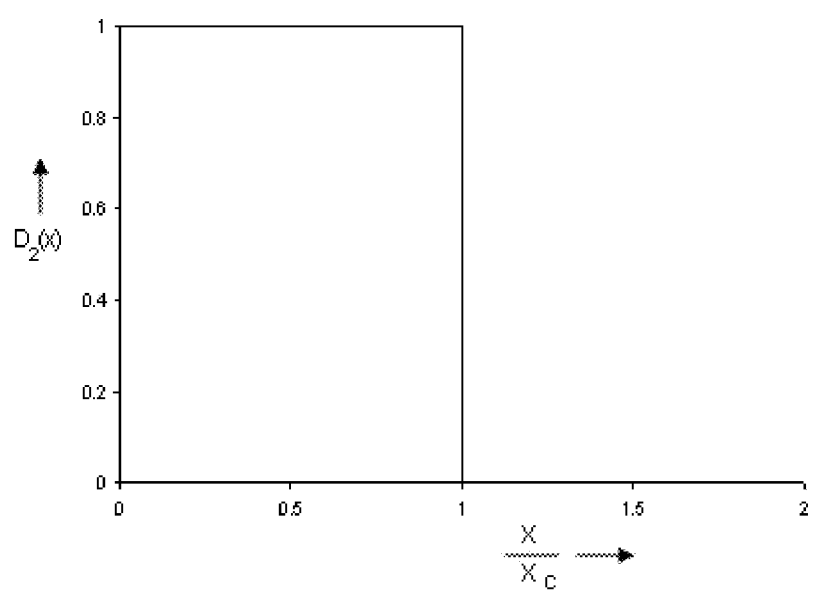
FIG. 5b is a discrete function converting information into scores for $D_1(x)$.
Figure 5C:
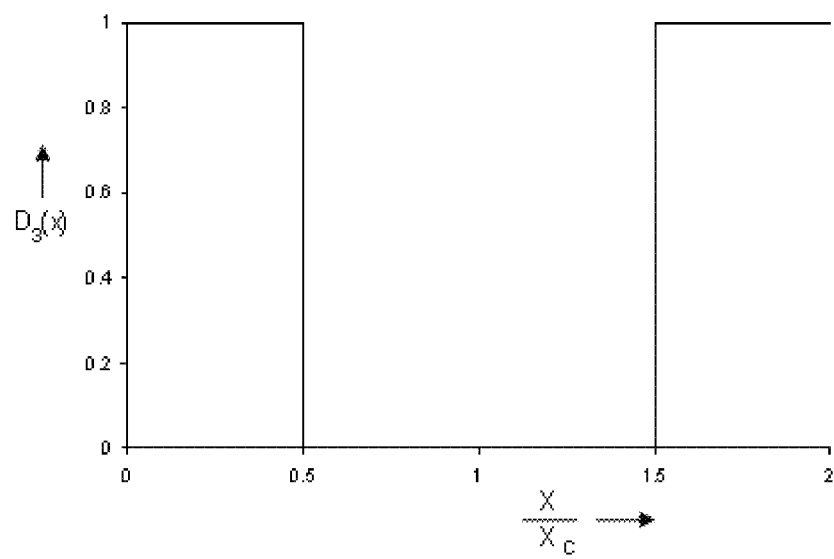
FIG. 5c is a discrete function converting information into scores for $D_2(x)$.
Figure 6A:
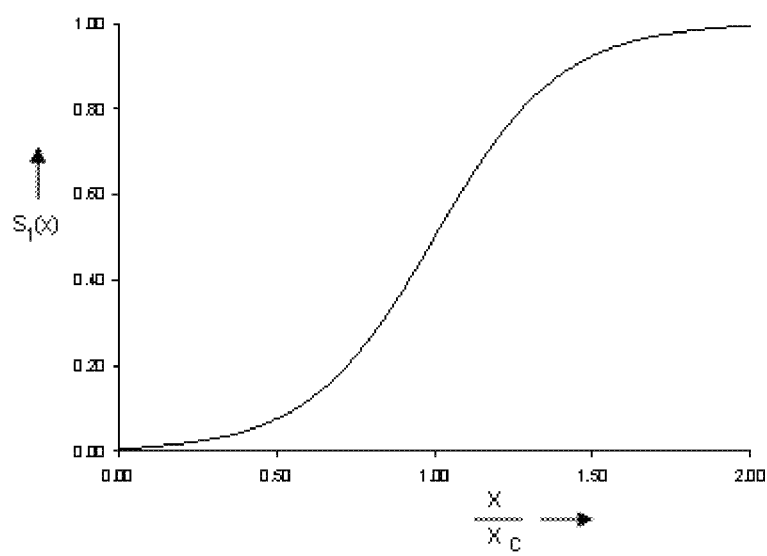
FIG. 6a is a continuous function converting information into scores for $S_1(x)$.
Figure 6B:
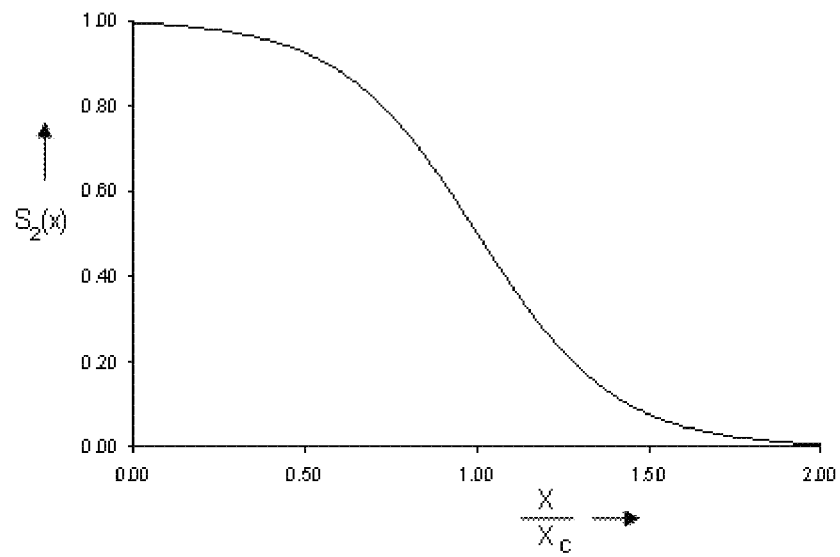
FIG. 6b is a continuous function converting information into scores for $S_2(x)$.
Figure 6C:
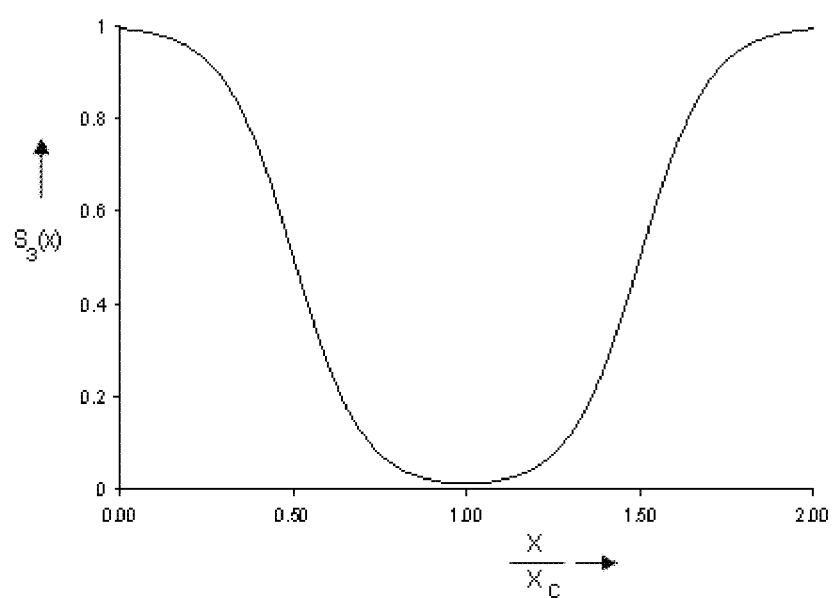
FIG. 6c is a continuous function converting information into scores for $S_3(x)$.

Functions D1 and S1, shown graphically in FIGS. 5a and 6a respectively, are designed to indicate that the amount of fluid removed should be increased when the value of the parameter increases, hence they are suitable for use with the parameters that have "positive correlations" to the fluid removal, which are the ones with "+" signs in the third column of Table 1. Opposite is true for the score functions D2 and S2, shown graphically in FIGS. 5b and 6b respectively, where amount of fluid removed should be decreased when the value of the parameter increases, hence they are suitable for use with the parameters that have negative correlations to the fluid removal, which are the ones with "−" signs in the third column of Table 1. Functions D3 and C3, shown graphically in FIGS. 5c and 6c respectively, produce high scores when the feature deviates from a central value, either by an increasing or by a decreasing deviation. They are provided for cases when parameter is supposed to be maintained within a range, such the serum potassium level.

Below is an example illustrating using the parameters and their conversion into raw scores. In this example, features P1 through P16 are as they were described in Table 1.
DFL=W1*S1(P1,C1,K1)+W2*S2(P2,C2,K2)+W3*S2(P3, C3,K3)+W4*S1(P4,C4,K4)+W5*S1(P5,C5,K5)+W6*S2 (P6,C6,K6)+W7*S2(P7,C7,K7)+W8*S2(P8,C8,K8)+ W9*S2(P9,C9,K9)+W10*S2(P10,C10,K10)+W12*S1(P12, C12,K12)+W13*S1(P13,C13,K13)+W14*S2(P14,C14, K14)+W15*S1(P15,C15,K15)+W16*S1(P16,C16,K16)

where the DLF is the recommended change for fluid removal; W1, W2, ..., W16 are the weighting coefficients; S1 and S2 are the functions are as defined in Table 2; P1, P2, ..., P16 are as defined in Table 1; C1, C2, ..., C16 are off-set coefficients, and K1, K2, ..., K16 are scaling coefficients.

In certain embodiments, the above computation can be called one form of a forward algorithm using information from Categories 1, 2 and 3, and producing the recommended change in the fluid removal. The offset coefficients can be determined and set so that the coefficients will equal the measured parameter when the parameter indicates no recommended change in fluid level. For example, if a patient's respiratory rate is 17 bpm in the absence of an excess of fluid, then the offset coefficient may be set at 17 bpm. The weighting coefficients can be set to give more weight to the parameters that are more indicative of a need to change the patient's fluid level, and to convert the numerical result of the function into a recommended change in patient fluid level in volume. If it is found in a particular patient that a particular parameter is not changing with a reduction in fluid level, and is found not to correlate to the patient outcome, then the weighting coefficient can be reduced to 0. This would eliminate that parameter from the algorithm. The scaling coefficients are set to determine the slope of the function. If a small change in the input parameter is highly indicative of a need to change patient fluid level, the slope of the function should be steep. If slight deviations in the input parameter are not highly indicative of a need to change patient fluid level, the slope of the function should be shallow.

For the calculation of the recommended change, weighting coefficients and the off-set and scaling coefficients can be determined. The constants as described herein are collectively denoted with the symbol M. These constants can be predetermined and adjusted by medical professionals attending the patient. Alternatively, the computing unit may adjust these constants based on the patient outcomes, using a backward algorithm. By utilizing the backward algorithm, the effect of changing patient fluid level can be correlated back to the individual parameters. From this, the proper weighting and scaling coefficients may be determined.

Table 3 provides nominal values for each of the 13 measured parameters listed. These values may be set as the offset coefficients in the initial determination of the constants M. Deviations from these values may be indicative of a need to change the patient's fluid level. In one embodiments, a computer can calculate the constants using the backward algorithm wherein the constants may be updated and/or changed. Additionally, the patient's medical history may show reasons for other than excess fluid that can cause a deviation from these values. When initially setting the constants for the patient's initial dialysis, the offset coefficients may be changed to reflect the deviations.

Figure 7:
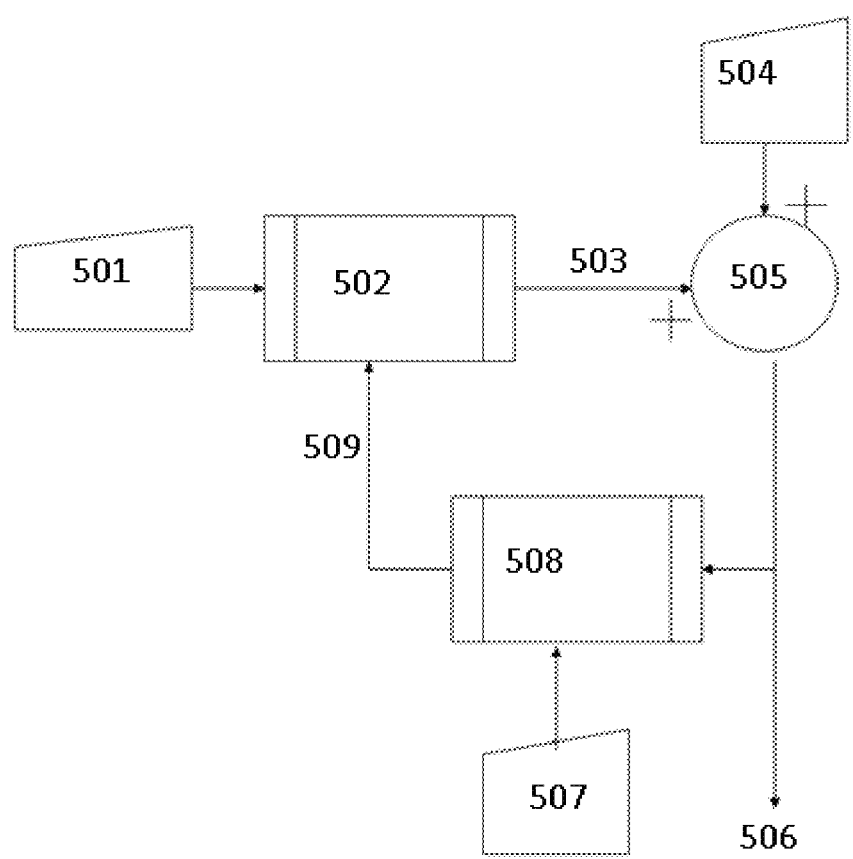
FIG. 7 is a block diagram showing the utilization of the data used by the present invention.

In certain embodiments, a computing unit can work to identify the constants M using the backward algorithm wherein the operation if the unit in the overall system is shown in FIG. 7. The information set 501 is fed into the forward algorithm 502 to produce the recommended change in the fluid removal 503. This value can be added to the fluid removed during the past dialysis session, 504, or P11 in Table 1, to produce the desired ultrafiltrate, UF, value 505, which is sent to the hemodialysis clinic 506. Clinical condition of the patient 507, or P16 in Table 1, can be monitored over time, and as required the coefficients M 509 are adjusted by the backward algorithm 508. The backward algorithm can be constructed using the many known statistical and signal processing methods, such as the least squares and steepest descent methodology. The backward algorithm may use data from more than one patient's dialysis session to modify the coefficient set M where there is a general correlation. Additionally, the backward algorithm can use the data from more than one dialysis session for the same patient.

In certain embodiments, for the initial use by each patient, the weighting, off-set and scaling coefficients can be derived and added to the system. These coefficients can be estimated by the user, or they may be based upon values that are found suitable for similar patients. Once dialysis begins, the forward algorithm will determine a recommended change in patient fluid level. At the same time, the patient outcome can be monitored using the backward algorithm, which will make changes to the coefficients.

The technical benefit of the adjustments to the coefficients by the backward algorithm and the adjustments to the recommended fluid level of the patient is a dynamic process that cannot be accomplished with pen and paper. The changes to the coefficients and therefore the changes to the recommended fluid level occur constantly in order to continuously update the recommended fluid level. These changes occur too quickly for the calculations to be performed with the use of pen and paper.

The processors described herein can be medical device processors. Medical device processors can control the collection of external or implantable medical device data, control the collection of metadata based on the collected data, and synchronize the data on a timeline. The computing unit and the sensors which detect the data in each of the categories are specific purpose computers and processors configured or a medical or healthcare setting. The computers or processors can have shielded circuitry to prevent electric shock to a patient or operator. In any embodiment, the computers and processors of the present invention are not general purpose computers and can have regulatory approval for approved medical use on patients. The processors also have communication systems, hardware and software that protect patient privacy by protecting the information obtained from the patient.

The systems described herein can also obtain historical data from electronic medical records or other sources. The hardware configurations of the system allow for transmission of the data obtained to the patient's electronic medical records, or to a hospital data hub, handheld device, or monitor. The computers or processors described herein are specially adapted to receive patient data from the sensors and immediately perform the necessary calculations to determine a new recommended fluid level.

One of ordinary skill in the art will realize that not all sixteen parameters are necessary in order to obtain a recommended change in patient fluid level. Each of the parameters individually tend to show whether a change in fluid level is necessary and by how much. Therefore, an accurate measurement of the recommended change in patient fluid level may be achieved using significantly less than all of the parameters. Additionally, other parameters may be found that also tend to show a need to change the patient's fluid level. One of ordinary skill in the art will realize that additional parameters may be utilized without exceeding the scope of the invention.

The recommended change in fluid level when the number of parameters used is not 16 would be given by the equation:

$$DFL = \sum_{i=1}^{n} Wi * Sx(Pi, Ci, Ki)$$

Where DFL is the recommended change in fluid level; W1 . . . Wn are the weighting coefficients; P1 . . . Pn are the parameters as defined in Table 1; C1 . . . Cn are off-set coefficients; K1 . . . Kn are scaling coefficients; and Sx is the appropriate function as defined in Table 2 for the given parameter Px. If the value of the given parameter is positively correlated to a need to change the patient fluid level, function S1 would be used. If the value of a given parameter is negatively correlated with a need to change patient fluid level, then S2 is the appropriate function. If deviations in the parameter in either direction from some off-set point indicate a need to change patient fluid level, then S3 is the appropriate function. For example, a system can be set up where the parameters utilized are AF burden, tissue impedance, heart rate variability, sleep pattern and body weight. The off-set coefficients would be set in the ranges shown in Table 3. Initially, the weighting coefficients and scaling coefficients would need to be estimated, but as the patient undergoes treatment, the backward algorithm will adjust these coefficients. Because there is no gray scale when using the discrete functions D1, D2 and D3, the only variable is the cut-off trigger Xc. For using the discrete functions D1, D2, and D3, the off-set coefficients should be chosen at some point beyond the normal value. This allows slight variations in the measured parameters before the function switches from giving a value of 0 to giving a value of 1. For example, if the patient's respiratory rate is 13 bpm in the absence of fluid accumulation, then the cut-off trigger could be set at 17 bpm, which allows some variation in respiratory rate without changing the result of the function.

In some embodiments of the invention, a communication system can be used. The communication system allows transferring data, including the information in the category 3 information source, recommended ultrafiltration amounts, and the coefficients M.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

TABLE 1

| Parameter Number | Parameter Name | Parameter Source | Example Source | Parameter correlation to fluid removal |
|---|---|---|---|---|
| P01 | AF Burden | Implantable/ wearable device | Implantable monitor LINQ manufactured by Medtronic | + |
| P02 | Tissue Impedance | Implantable/ wearable device | Implantable monitor LINQ manufactured by Medtronic | − |
| P03 | Ambulatory HRV | Implantable/ wearable device | Implantable monitor LINQ manufactured by Medtronic | − |
| P04 | Respiratory Rate | Implantable/ wearable device | Derived from P02 using a real time algorithm | + |
| P05 | Sleep pattern (nocturnal activity) | Implantable/ wearable device | Implantable monitor LINQ manufactured by Medtronic or Zeo, Fitbit and Lark. | + |
| P06 | Body temperature | Implantable/ wearable device | LINQ or any other electronic thermometer. | − |
| P07 | Heart rate change during dialysis | Dialysis System/ Implant | Derived from P03 or any ECG monitor | − |
| P08 | HRV during the dialysis session | Dialysis System/ Implant | Derived from P03 or any ECG monitor | − |
| P09 | BP reduction during dialysis | Dialysis System | BP meter with connectivity, e.g. Omron 10+ or Medron. | − |
| P10 | Mixed venous oxygen saturation | Dialysis System | Edwards Swan-Ganz Oximeter | − |
| P11 | Fluid removed during dialysis session | Dialysis System | Fresenius 2008k | None |
| P12 | Dialysis markers measured periodically | Dialysis Clinic | Nova Model 16 Electrolyte Analyzer | + |
| P13 | Patient weight measured | Dialysis Clinic | LifeSpan DS 1000i Digital Scale | + |
| P14 | Medications and their dosage | Manual entry or EMR transfer | AthenaHealth EHR | − |

TABLE 1-continued

| Parameter Number | Parameter Name | Parameter Source | Example Source | Parameter correlation to fluid removal |
|---|---|---|---|---|
| P15 | Patient supplied data (discomfort) | Manual entry | MyMedical App for iPhone | + |
| P16 | Clinical data | Manual entry or EMR transfer | AthenaHealth her | + |

TABLE 2

| Name | Mathematical Expression |
|---|---|
| D1 | $D_1(x, x_C) = \begin{cases} 1, & x > x_C \\ 0, & x \leq x_C \end{cases}$ |
| D2 | $D_2(x, x_C) = \begin{cases} 0, & x > x_C \\ 1, & x \leq x_C \end{cases}$ |
| D3 | $D_3(x, x_C) = \begin{cases} 1, & |x| > x_C \\ 0, & |x| \leq x_C \end{cases}$ |
| S1 | $S_1(x, x_C, k) = \dfrac{1}{1 + e^{k(x_C - x)}}$ |
| S2 | $S_2(x, x_C, k) = \dfrac{1}{1 + e^{k(x - x_C)}}$ |
| S3 | $S_3(x, x_C, k) = \dfrac{1}{1 + e^{k\left(\frac{3}{2}x_C - x\right)}} + \dfrac{1}{1 + e^{k\left(x - \frac{x_C}{2}\right)}}$ |

TABLE 3

| Parameter Number | Parameter Name | Nominal Value | Reference |
|---|---|---|---|
| P01 | AF Burden | Episodes <5 min AF <1% of time | http://crm.cardiosource.org/Learn-from-the-Experts/2013/09/DeviceDetected-AFib-and-Stroke-Risk.aspx?print=1 |
| P02 | Tissue Impedance | Median value measured 10 wks after implant. | Internal data |
| P03 | Ambulatory HRV | Peak occurs in the 0.15-0.40 Hz range | |
| P04 | Respiratory Rate | 10-15 breaths/min | |
| P05 | Sleep pattern (nocturnal activity) | REM - nonREM alternating 90 min | http://learn.chm.msu.edu/neuroed/neurobiology_disease/content/otheresources/sleepdisorders.pdf |
| P06 | Body temperature | 36-38 Celsius | |
| P07 | Heart rate change during dialysis | 5 bpm | |
| P08 | HRV during the dialysis session | Peak occurs in the 0.15-0.40 Hz range | |
| P09 | BP reduction during dialysis | 10 mmHg | |
| P10 | Mixed venous oxygen saturation | 69 +/− 1 mmHg | |
| P11 | Fluid removed during dialysis session | 1.5 Liters | |
| P12 | Dialysis markers measured periodically | K = 3-5 mM | |
| P13 | Patient weight measured | Change <2 kg | |
| P14 | Medications and their dosage | | |
| P15 | Patient supplied data (discomfort) | | |
| P16 | Clinical data | | |

We claim:

1. A method, comprising the steps of:

obtaining one or more parameters correlated for fluid removal from a patient connected to a first medical device configured to obtain the one or more parameters;

transferring data for the one or more parameters to a medical device processor wherein the medical device processor utilizes the one or more parameters in a forward algorithm to generate a recommended fluid level, the medical device processor determining the recommended fluid level; and adjusting fluid removal via a second medical device from the patient based on the recommended fluid level;

wherein the forward algorithm is presented by the equation:

$$DFL = \sum_{i=1}^{n} Wi * Sx(Pi, Ci, Ki)$$

where Wi is a weighting coefficient predetermined according to a level of impact on fluid removal by a corresponding parameter (Pi), Ci is an off-set coefficient predetermined when a corresponding parameter Pi indicates no recommended change in fluid level, Ki is a scaling coefficient predetermined according to a slope of change in fluid removal by a corresponding parameter Pi, and where Sx is one of S1, S2, and S3, S1 is a function with an output between 0and 1 and increases from 0 to 1 as Pi increases in value, S2 is a function with an output between 0 and 1 and deceases from 1 to 0 as Pi increases in value, S3 is a function with an output between 0 and 1 and increases from 0 to 1 as Pi varies in value from a set point, Sx is S1 when Pi is positively correlated to fluid removal, Sx is S2 when Pi is negatively correlated to fluid removal, Sx is S3 when Pi correlates to fluid removal as it deviates from the set point.

2. The method of claim 1, wherein the step of obtaining includes obtaining one or more parameters positively correlated for fluid removal and one or more parameters negatively correlated for fluid removal, wherein the medical device processor processes the one or more positively correlated parameters using a first function and processes the one or more negatively correlated parameters using a second function.

3. The method of claim 2, wherein the one or more parameters positively correlated for fluid removal are selected from the group consisting of atrial fibrillation burden, respiratory rate, sleep pattern, dialysis markers, patient weight, patient medications and dosage, patient supplied data indicative of fluid removal, and clinical data indicative of fluid removal.

4. The method of claim 2, wherein the one or more parameters negatively correlated for fluid removal are selected from the group consisting of tissue impedance, ambulatory heart rate variability, body temperature, heart rate change during dialysis, heart rate variability during dialysis, blood pressure reduction during dialysis, mixed venous oxygen saturation, and patient medications and dosage indicative of fluid retention.

5. The method of claim 2, wherein the one or more parameters positively correlated for fluid removal include pulmonary arterial pressure, venous pressure, and atrial pressure.

6. The method of claim 1, wherein the one or more of the parameters are obtained from the patient prior to dialysis.

7. The method of claim 1, wherein one or more of the parameters are obtained from measurements made during dialysis.

8. The method of claim 1, wherein one or more of the parameters are obtained from the patient's medical records.

9. The method of claim 1, wherein the parameters are atrial fibrillation burden, tissue impedance, heart rate variability, sleep pattern and body weight.

10. The method of claim 1, further comprising the step of changing the fluid level in the patient to the recommended fluid level by ultrafiltration.

11. The method of claim 1, further comprising adjusting the weighting coefficient, the off-set coefficient and the scaling coefficient during dialysis by using a backward algorithm, wherein the backward algorithm utilizes data from two or more dialysis sessions of the patient.

12. The method of claim 1, wherein the step of connecting includes obtaining a category one parameter from an implantable device and a category two parameter from a dialysis session.

13. The method of claim 12, wherein the step of obtaining further includes obtaining a category three parameter from a medical device different from the implantable device.

14. The method of claim 12, wherein the step of transferring data includes transferring at least one parameter of a category to a first data area in the medical device processor and transferring the parameter of a category to a second data area in the medical device processor, and wherein the first and second data areas received by the medical processor are implemented using the forward algorithm.

15. The method of claim 1, wherein the medical device processor continuously updates the recommended fluid level using a backward algorithm during a dialysis session.

16. The method of claim 1, wherein the one or more parameters include at least one of serum creatinine level and BNP level.

17. A system, comprising:
a first medical device to generate one or more parameters correlated for fluid removal in a patient;
a medical device processor; wherein the first medical device transfers data for the one or more parameters to the medical device processor, wherein the medical device processor programmed with a forward algorithm to generate a recommended fluid level in the patient, the medical device processor determining the recommended fluid level; and
a second medical device to adjust fluid removal from the patient based on the recommended fluid level;
wherein the forward algorithm is presented by the equation:

$$DFL = \sum_{i=1}^{n} Wi * Sx(Pi, Ci, Ki)$$

where Wi is a weighting coefficient predetermined according to a level of impact on fluid removal by a corresponding parameter (Pi), Ci is an off-set coefficient predetermined when a corresponding parameter Pi indicates no recommended change in fluid level, Ki is a scaling coefficient predetermined according to a slope of change in fluid removal by a corresponding parameter Pi, and where Sx is one of S1, S2, and S3, S1 is a function with an output between 0and 1 and increases from 0 to 1 as Pi increases in value, S2 is a function with an output between 0 and 1 and deceases from 1 to 0 as Pi increases in value, S3 is a function with an output between 0 and 1 and increases from 0 to 1 as Pi varies in value from a set point, Sx is S1 when Pi is positively correlated to fluid removal, Sx is S2 when Pi is negatively correlated to fluid removal, Sx is S3 when Pi correlates to fluid removal as it deviates from the set point.

18. The system of claim 17, wherein the forward algorithm computes by utilizing one or more parameters positively correlated for fluid removal and one or more parameters negatively correlated for fluid removal.

19. The system of claim 18, wherein the one or more parameters positively correlated for fluid removal are selected from the group consisting of atrial fibrillation burden, respiratory rate, sleep pattern, dialysis markers, patient weight, patient medications and dosage, patient supplied data indicative of fluid removal, and clinical data indicative of fluid removal.

20. The system of claim 18, wherein the one or more parameters positively correlated for fluid removal are selected from the group consisting of pulmonary arterial pressure, venous pressure, and atrial pressure.

21. The system of claim 18, wherein the one or more parameters negatively correlated for fluid removal are selected from the group consisting of tissue impedance, ambulatory heart rate variability, body temperature, heart rate change during dialysis, heart rate variability during dialysis, blood pressure reduction during dialysis, mixed venous oxygen saturation, and patient medications and dosage indicative of fluid retention.

22. The system of claim 17, wherein n is between 5 and 100.

23. The system of claim 17, wherein the first medical device includes an implantable device and the second medical device includes a dialyzer.

24. The system of claim 17, further comprising a signaling mechanism to signal when there is a recommended change in the patient's fluid level.

25. The system of claim 17, wherein the medical device processor continuously updates the recommended fluid level using a backward algorithm during a dialysis session.

26. The system of claim 17, wherein the one or more parameters include at least one of serum creatinine level and BNP level.

* * * * *